US005336207A

United States Patent [19]

Norcia

[11] Patent Number: 5,336,207

[45] Date of Patent: Aug. 9, 1994

[54] METHOD FOR REMOVAL OF MEDICAL ADHESIVE FROM SKIN

[75] Inventor: Michael A. Norcia, Safety Harbor, Fla.

[73] Assignee: Smith & Nephew United Inc., Largo, Fla.

[21] Appl. No.: 26,867

[22] Filed: Mar. 5, 1993

Related U.S. Application Data

[63] Continuation of Ser. No. 838,466, Feb. 19, 1992, abandoned.

[51] Int. Cl.$^5$ .............................................. A61M 35/00

[52] U.S. Cl. .................................... 604/290; 604/289; 106/901; 252/364; 128/898

[58] Field of Search ................ 128/898; 604/289, 290, 604/303, 310, 336, 344, 2, 3; 106/901; 252/364

[56] References Cited

U.S. PATENT DOCUMENTS 2,999,265 9/1961 Duane et al. .......................... 15/506
4,673,524 6/1987 Dean .................................. 252/118
5,004,502 4/1991 Ramzan .......................... 106/287.13

OTHER PUBLICATIONS

Hawley's, Condensed Chemical Dictionary, 11th Ed., (1987), pp. 788 and 806.

*Industrial Solvents Handbook,* 2nd ed. New Jersey, Noyes Data Corporation, 1977, pp. 71, 365, 366, 380, and 383.

*Primary Examiner*—Randall L. Green
*Assistant Examiner*—Paul Prebilic
*Attorney, Agent, or Firm*—Rosenman & Colin

[57] ABSTRACT

A method for removal of a medical adhesive from the skin without irritation to the skin comprises applying to the medical adhesive on the skin an adhesive cleansing solvent comprising can oxyalylene alkyl ether such as dipropylene glycol monomethyl ether and a liquid aliphatic hydrocarbon such as a mixture of $C_{10-11}$ paraffins.

12 Claims, No Drawings

METHOD FOR REMOVAL OF MEDICAL ADHESIVE FROM SKIN

CROSS-REFERENCE

This is a continuation of Ser. No. 838,466 filed Feb. 19, 1992, now abandoned.

This invention relates to a method for removal of a medical adhesive from the skin which comprises applying to the medical adhesive on the skin an adhesive cleansing solvent.

Adhesives are routinely employed to secure medical devices such as non-adherent dressings and catheters to the skin as well as for adhesive dressings. Removal of the device or dressing may leave residual traces of adhesive on the skin. Adhesive residues can be a nuisance particularly if it is required to re-affix a device at the same skin site. Moreover skin trauma may occur when an adhesively secured device is removed. Solvents are traditionally used to facilitate removal of both the adhesive product or device and any remaining residues.

Many solvents act as defatting agents and can cause skin irritation. Irritation and skin trauma is especially prevalent where adhesive products have to be applied repeatedly to the same skin site.

Additionally many of the traditional solvents are flammable and are considered to be dangerous safety hazards.

The most common types of medical pressure sensitive adhesives used for attachment to the skin are based upon two different molecular species. These are the polyisobutylene polymers and polyacrylate copolymers. Typical formulae for polyisobutylene based adhesive systems used for medical devices are described in U.S. Pat. Nos. 3,339,546 and 4,253,460. Polyacrylate adhesives frequently applied to the skin in the form of plastic tapes, bandages, transdermal medical delivery systems and the like are described in U.S. Pat. Nos. 3,691,140 and 4,420,470.

The polyisobutylene polymers have a solubility parameter of about 7.5 cal ½/cm 3/2 (reference CRC *Handbook of Solubility Parameters and Other Cohesion Parameters*, Barton, 4th Edition 1988, pg 282). The polyacrylate adhesives exhibit approximate solubility parameters of 12 to 13 cal ½cm 3/2. Due to the significant difference in solubility parameters between polyisobutylene polymers and the polyacrylate copolymers it would be expected that different incompatible solvent systems would be required to dissolve either of the two polymers. Thus, polyisobutylene is readily soluble in solvents such as hexane or toluene whereas the polyacrylates are readily soluble in esters such as ethyl acetate or ketones such as methyl ethyl ketone. We have now found that the disadvantages of the prior can be mitigated by the use of a single solvent. This invention criers one simple solvent system containing medically safe solvents capable of aiding the removal of adhesive medical devices and their associated adhesive residue from the skin irrespective of whether the adhesive is a polyisobutylene based system or a polyacrylate copolymer based system.

Accordingly, the present invention provides a method for removal of a medical adhesive from the skin without irritation to the skin, which comprises applying to the medical adhesive on the skin an adhesive cleansing solvent comprising an oxyalkylene alkyl ether and a liquid aliphatic hydrocarbon.

Aptly the solvent will have a flash point higher than 100° F.

The liquid aliphatic hydrocarbon for use in the invention aptly comprises paraffins having an alkyl chain of at least 6 carbon atoms. Favourable the liquid aliphatic hydrocarbon will comprise paraffin having alkyl chains of not more than 17 carbon atoms. Suitably the hydrocarbon liquid will comprise paraffins having about 10 or 11 carbon atoms per molecule. A suitable hydrocarbon for use in the invention is heptane. Preferably the aliphatic hydrocarbon will be a mixture of paraffins comprising isoparaffins. Preferred hydrocarbon components will have a flash point of greater than 100° F. A favoured liquid aliphatic hydrocarbon is that sold under the trade name ISOPAR G. This is material is a narrow cut isoparaffinic hydrocarbon mixture with a boiling range of 155°-176° C. and is produced by the Exxon Company. Aptly the ether component of the solvent may be an alkyl ether in which the alkyl group is a lower alkyl group. More preferably the alkyl group has up to four carbon atoms.

The glycol ether may be a monoether or a polyether. Aptly the ether is a diether or a triether. However, more aptly the ether will be a monoether.

The oxyalkylene group of the ether is aptly lower, oxyalkylene, more aptly an alkylene group containing up to 4 carbon atoms. Suitably the alkylene group will be oxypropylene.

A preferred ether for use in the invention is dipropylene glycol monomethyl ether.

A preferred adhesive cleaning solvent in accordance with the invention consists essentially of a mixture of dipropylene glycol monomethyl ether and an isoparaffinic $C_4$-$C_{11}$ hydrocarbon.

The ratio of ether to aliphatic hydrocarbon can vary over a wide range. Aptly the adhesive cleaning solvent of the invention can comprise from 20 to 90% by weight of the ether component and from 80 to 10% by weight of the hydrocarbon component. Suitably the solvents will comprise from 40 to 70%, more suitably from 45 to 65% by weight of the ether component and from 60 to 30%, more suitably from 45 to 55% by weight of the hydrocarbon component.

A preferred adhesive cleansing solvent of the invention comprises dipropylene glycol monomethyl ether and ISOPAR G in approximately equal amounts by weight. Solvent of this formulation has a solubility parameter of 8.0 cal ½/cm 3/2 and will effectively remove both polyisobutylene and polyacrylate based adhesives from the skin with essentially no skin trauma occurring.

The adhesive cleansing solvents of the invention may contain other additives such as preservatives, anti-oxidants, fragrances and skin protectants.

The invention will now be illustrated by the following examples.

EXAMPLE 1

An adhesive cleansing solvent was produced according to the following formulation:

| Component | % Wt/Wt | Function |
|---|---|---|
| Arcosolv (R) DPM (Dipropylene Glycol Methyl Ether) | 49.900 | Solvent |
| Isopar G (Isoparaffinic Solvent) | 48.575 | Solvent |
| Aloe Extract | 1.250 | Skin |

-continued

| Component | % Wt/Wt | Function |
|---|---|---|
| | | Protectant |
| Givaden ESC 10,740 (0.05%) | 0.075 | Fragrance |
| Belmay 10139-186 (.025%) | | |
| Benzyl Alcohol | 0.10 | Preservative |
| Butylated Hydroxyanisole (B.H.A.) | 0.10 | Anti-oxidant |

This formulation was used to determine its ability to sensitize human skin using the following test procedure.

A 2 $cm^2$ test site was outlined with a gentian violet skin market on the infrascapular region of the back. A clean, cotton swab was dipped into the formulation and applied immediately to the test site and rubbed for 15 seconds.

The test site was then wiped with a wet gauze pad, dried and covered with an occulusive patch formed from a gauze pad covered with a plastic film adhesive tape. The patch was removed after 24 hours and the test procedure repeated a further 24 hours later. After six repetitions of the test, the area within the area of the skin marking was evaluated for both erythema and edema formulations using the Draize test (Draize, J. H. 1959 Dermal Toxicity, pages 46-59 in Appraisal of the Safety of Chemicals in Goods, Drugs and Cosmetics, The Association of Food and Drug Officials of the United States, Bureau of Food and Drugs, Austin, Tex., U.S.A.).

In over 100 separate tests a temporary barely perceptible erythema was observed in only one case during the induction phase and during the challenge phase no erythema was observed in any of the subjects.

EXAMPLE 2

Formulations were prepared as described in Example 1 except that the ratio of the ether and hydrocarbon components was varied as shown in the following table, The efficacy of the solvent for removing adhesive for each of polyisobutylene and polyacrylate adhesives is expressed as an integer on a scale of 0 to 4.

| Arcosolv (%) | Isopar (%) | Efficacy Isobutylene | Acrylate |
|---|---|---|---|
| 30 | 70 | 3 | 1 |
| 40 | 60 | 3 | 2 |
| 50 | 50 | 4 | 4 |
| 60 | 40 | 3 | 1 |
| 70 | 30 | 2 | 1 |
| 80 | 20 | 2 | 1 |

Scale
0 no solvent effect
1 minimal solvent effect
2 moderate solvent effect
3 good solvent effect
4 excellent solvent effect

I claim:

1. A method for removal of a medical adhesive from skin without irritation to the skin, which comprises applying to the medical adhesive on the skin an adhesive cleansing solvent comprising an oxyalkylene alkyl ether and a liquid aliphatic hydrocarbon, rubbing the medical adhesive skin and removing the medical adhesive.

2. The method according to claim 1, wherein the medical adhesive on the skin is a polyisobutylene or a polyacrylate medical adhesive.

3. The method according to claim 1, wherein the adhesive cleansing solvent has a flash point greater than 100° F.

4. The method according to claim 1, wherein the liquid aliphatic hydrocarbon is a mixture of paraffins.

5. The method according to claim 4, wherein each paraffin contains from 6 to 17 carbon atoms.

6. The method according to claim 4, wherein the mixture of paraffins comprises a mixture of isoparaffins.

7. The method according to claim 1, wherein the oxyalkylene alkyl ether is an oxyalkylene mono alkyl ether in which the alkyl group contains 1 to 4 carbon atoms.

8. The method according to claim 7, wherein the oxyalkylene monoalkyl ether is an oxyalkylene monomethyl ether.

9. The method according to claim 1, wherein the alkylene group of the oxyalkylene alkyl ether contains 1 to 4 carbon atoms.

10. The method according to claim 1, wherein the oxyalkylene alkyl ether is dipropylene glycol monomethyl ether.

11. The method according to claim 1, wherein the adhesive cleansing solvent comprises from 20% to 90% by weight of said oxyalkylene alkyl ether and 80% to 10% by weight of a liquid aliphatic hydrocarbon.

12. A method for the removal of polyisobutylene or polyacrylate adhesives from skin without irritation to the skin, comprising applying to the polyisobutylene or polyacrylate adhesive on the skin an adhesive cleansing solvent consisting essentially of from 40% to 60% by weight of dipropylene glycol monomethyl ether and from 60% to 40% by weight of a liquid aliphatic hydrocarbon mixture comprising isoparaffins containing from 10 to 17 carbon atoms, rubbing the polyisobutylene or polyacrylate skin adhesive and removing the polyisobutylene or polyacrylate adhesive.

* * * * *